US010844435B1

(12) United States Patent
Vijayan

(10) Patent No.: US 10,844,435 B1
(45) Date of Patent: Nov. 24, 2020

(54) METHOD TO TREAT HYPOTENSION USING VASOPRESSIN IN CERTAIN GENOTYPES

(71) Applicant: Par Pharmaceutical, Inc., Chestnut Ridge, NY (US)

(72) Inventor: Saji Vijayan, Chester Springs, PA (US)

(73) Assignee: PAR PHARMACEUTICAL, INC., Chestnut Ridge, NY (US)

( * ) Notice: Subject to any disclaimer, the term of this patent is extended or adjusted under 35 U.S.C. 154(b) by 0 days.

(21) Appl. No.: 16/932,351

(22) Filed: Jul. 17, 2020

(51) Int. Cl.
  *C12Q 1/6883* (2018.01)
  *A61P 9/02* (2006.01)
  *A61K 38/095* (2019.01)

(52) U.S. Cl.
  CPC .......... *C12Q 1/6883* (2013.01); *A61K 38/095* (2019.01); *A61P 9/02* (2018.01); *C12Q 2600/106* (2013.01)

(58) Field of Classification Search
  CPC ... C12Q 1/6883; C12Q 2600/106; A61P 9/02; A61K 38/095
  See application file for complete search history.

(56) References Cited

U.S. PATENT DOCUMENTS

| | | | | |
|---|---|---|---|---|
| 9,375,478 | B1 * | 6/2016 | Kenney | A61K 47/10 |
| 9,687,526 | B2 * | 6/2017 | Kenney | A61K 38/22 |
| 9,744,209 | B2 * | 8/2017 | Kenney | A61K 47/02 |
| 9,744,239 | B2 * | 8/2017 | Kenney | A61K 47/10 |
| 9,750,785 | B2 * | 9/2017 | Kenney | G01N 30/88 |
| 9,919,026 | B2 * | 3/2018 | Kenney | A61K 31/045 |
| 9,937,182 | B2 * | 4/2018 | Grobe | A61K 31/404 |
| 9,937,223 | B2 * | 4/2018 | Kenney | A61K 47/02 |
| 2009/0298711 | A1 * | 12/2009 | Russell | C12Q 1/6883 506/16 |
| 2015/0374698 | A1 | 12/2015 | Grobe et al. | |
| 2015/0377876 | A1 | 12/2015 | Grobe et al. | |
| 2018/0228806 | A1 | 8/2018 | Grobe et al. | |

OTHER PUBLICATIONS

Argenziano et al.; "A prospective randomized trial of arginine vasopressin in the treatment of vasodilatory shock after left ventricular assist device placement;" Circulation; 1997; 96 (9 Suppl); pp. 286-290.
Choong et al.; "Vasopressin in pediatric shock and cardiac arrest;" Pediatr Crit Care Med; 2008; 9; pp. 372-379.
Holmes et al.; "Science review: Vasopressin and the cardiovascular system part 1-receptor physiology;" Crit Care; 2003; 7; pp. 427-434.
Jochberger et al.; "The vasopressin and copeptin response to infection, severe sepsis, and septic shock;" Crit Care Med; 2009; 37; pp. 476-482.
Landry et al.; Vasopressin Deficiency Contributes to the Vasodilation of Septic Shock, Circulation; 1997; 95; pp. 1122-1125.
Landry et al.; "The pathogenesis of vasodilatory shock;" N Engl J Med; 2001; 345; pp. 588-595.
Levin et al.; "Association between arginine vasopressin 1a receptor (AVPR1a) promoter region polymorphisms and prepulse inhibition;" Psychoneuroendocrinology; 2009; 34(6) p. 901-908.
Matsumoto et al.; "Characterization of a recombinant soluble form of human placental leucine aminopeptidase/oxytocinase expressed in Chinese hamster ovary cells;" Eur J Biochem; 2000; 267(1); pp. 46-52.
Mekontso-Dessap et al.; "Risk factors for post-cardiopulmonary bypass vasoplegia in patients with preserved left ventricular function;" Ann Thorac Surg; 2001; 71(5); pp. 1428-1432.
Möhring et al.; "Greatly enhanced pressor response to antidiuretic hormone in patients with impaired cardiovascular reflexes due to idiopathic orthostatic hypotension;" J Cardiovasc Pharmacol; 1980; 2(4); pp. 367-376.
Moses et al.; "Urinary and metabolic clearances of arginine vasopressin in normal subjects;" Am J Physiol;1986; 251 (Regulatory Integration Comp. Physiol. 20); pp. R365-R370.
Nakada et al. "Leucyl/cystinyl aminopeptidase gene variants in septic shock;" Chest; 2011; 139(5); pp. 1042-1049.
Russell J.; "Vasopressin in vasodilatory and septic shock;" Curr Opin Crit Care; 2007; 13; pp. 383-391.
Russell et. al.; "Vasopressin versus Norepinephrine infusion in patients with septic shock;" N Engl J Med; 2008; 358 (9) pp. 877-887.
Vasostrict (vasopressin injection, USP) [package insert]. Par Pharmaceutical Companies, Inc.; Chestnut Ridge (NY); 2019, 2 pages.
Wallis et al.; "Vasopressin is a physiological substrate for the insulin-regulated aminopeptidase IRAP;" Am J Physiol Endocrinol Metab; 2007; 293(4); pp. E1092-E1102 (first published on Aug. 7, 2007).
Ramirez-Expósito et al.; "A PCR-RFLP method for detection of the LNPEP encoding human insulin-regulated aminopeptidase (IRAP) rs4869317 polymorphism;" Indian J Med Res.; Jul. 2016; 144(1); pp. 120-123.
Kondo et al.; "The clinical course and pathophysiological investigation of adolescent gestational diabetes insipidus: a case report;" BMC Endocrine Disorders; Jan. 30, 2018; 18(1):4 (8 pages); doi: 10.1186/s12902-018-0234-6.
"The Use of Vasopressin for Septic Shock;" date May 6, 2003, accessed online at http://www.surgicalcriticalcare.net/Guidelines/vasopressin.pdf on Jul. 3, 2020. (Year: 2003).
Hajjar et al.; "Vasopressin versus Norepinephrine in Patients with Vasoplegic Shock after Cardiac Surgery;" Anesthesiology, vol. 126, pp. 85-93. (Year: 2017).
Anantasit et al.; "Serious Adverse Events Associated with Vasopressin and Norepinephrine Infusion in Septic Shock;" Critical Care Medicine, 2014. vol. 42, No. 8, pp. 1812-1820. (Year: 2014).
Kristensen et al.; "High-throughput methods for detection of genetic variation;" BioTechniques; Feb. 2001; 30:318-332.
Tsuchihashi et al.; "Progress in high throughput SNP genotyping methods;" The Pharmacogenomics Journal; (2002) 2; pp. 103-110.
Edenberg et al.; "Chapter 16: Laboratory methods for high-throughput genotyping;" Cold Spring Harbor Laboratory Press; 2009; pp. 183-193.

(Continued)

*Primary Examiner* — Marcela M Cordero Garcia
(74) *Attorney, Agent, or Firm* — Mayer Brown LLP

(57) ABSTRACT

The present disclosure relates to a method of treating a patient experiencing hypotension, comprising genotyping for a TT, AA, or AT genotype, and administering a therapeutically effective amount of vasopressin based on genotype to maintain a target blood pressure.

6 Claims, 2 Drawing Sheets

(56) References Cited

OTHER PUBLICATIONS

Young et al.; "Deconstructing the sources of genotype-phenotype associations in humans;" Science; Sep. 27, 2019; 365(6460); pp. 1396-1400 (Author Manuscript; 18 pages).
Moses et al.; "Effects of Sodium Intake, Furosemide, and Infusion of Atrial Natriuretic Peptide on the Urinary and Metabolic Clearances of Arginine Vasopressin in Normal Subjects;" J Clin Endocrinol Metab; 1990; 70: 222-229.
Varpula et al.; "Hemodynamic variables related to outcome in septic shock;" Intensive Care Med (2005) 31:1066-1071.
Moman et al.; "Impact of individualized target mean arterial pressure for septic shock resuscitation on the incidence of acute kidney injury: a retrospective cohort study;" Ann. Intensive Care (2018) 8:124 (10 pages).

* cited by examiner

METHOD TO TREAT HYPOTENSION USING VASOPRESSIN IN CERTAIN GENOTYPES

TECHNICAL FIELD

The present invention relates to the field of treating hypotension and related conditions.

BACKGROUND

Vasopressin is a neurohypophyseal peptide hormone with diverse actions that are mediated by tissue-specific receptors, which are classified into V1 vascular, V2 renal, V3 pituitary, oxytocin, and P2 purinergic subtypes. The chemical name of vasopressin is Cyclo (1-6) L-Cysteinyl-L-Tyrosyl-L-Phenylalanyl-L-Glutaminyl-L-Asparaginyl-L-Cysteinyl-L-Prolyl-L-Arginyl-L-Glycinamide. The molecular formula is $C_{46}H_{65}N_{15}O_{12}S_2$ with a molecular weight of 1084.23 Da.

VASOSTRICT® (vasopressin injection, USP) was approved by the United States Food and Drug Administration in 2014 to increase blood pressure in adults with vasodilatory shock (e.g., post-cardiotomy or sepsis) who remain hypotensive despite treatment with fluids and catecholamines. VASOSTRICT® is a solution for intravenous (IV) administration available as 20 units/mL in a single dose vial and 200 units/10 mL (20 units/mL) in a multiple dose vial.

It is known in the art that overdosage with VASOSTRICT® can be expected to manifest as consequences of vasoconstriction of various vascular beds (peripheral, mesenteric, and coronary) and as hyponatremia. It was additionally known in the art that overdosage with VASOSTRICT® may lead less commonly to ventricular tachyarrhythmias (including Torsade de Pointes), rhabdomyolysis, and non-specific gastrointestinal symptoms.

The enzyme leucyl/cystinyl aminopeptidase ("LNPEP" or "vasopressinase") degrades vasopressin and is primarily responsible for the short (~4 to ~24 minute) half-life of vasopressin (Nakada et al., "*Leucyl/Cystinyl Aminopeptidase Gene Variants in Septic Shock*," Chest 139 (5): 1042-49 (2011)). For this reason, Nakada et al. hypothesized that genetic variations in the vasopressin pathway genes, including the gene that encodes for LNPEP, may cause a downstream clinical effect in patients experiencing septic shock. They screened available DNA from 616 septic shock patients who participated in the Vasopressin and Septic Shock (VASST) trial, a multicenter, randomized, double blind, controlled trial evaluating the efficacy of vasopressin versus norepinephrine (Russell et. al.; "*Vasopressin Versus Norepinephrine Infusion in Patients with Septic Shock*," N. Engl. J. Med. 358 (9): 877-887 (2008)). From these, Nakada and coworkers identified 230 single nucleotide polymorphisms (SNPs) and screened those for any association with mortality rate seen in the VASST trial. It was found that the major [T] allele of LNPEP rs4869317 [A/T] SNP correlated with an increase in the 28-day mortality. Id. From this, a major allele model (TT vs. AA/AT genotype) was established. Nakada et al. found that patients of the TT genotype appeared to have a higher hazard ratio compared with the AA or AT (a/k/a TA) genotyped patients and also appeared to have exhibited an increase in vasopressin clearance over the AA or AT genotyped patients.

Anantasit et al. ("*Serious Adverse Events Associated With Vasopressin and Norepinephrine Infusion in Septic Shock*," Crit. Care Med. 42 (8): 1812-20 (2014)) also analyzed patients from the above-referenced VASST trial. Anantasit hypothesized that SNPs of candidate genes of the vasopressin pathway and/or plasma arginine vasopressin (AVP) levels could predict serious adverse events in patients who had septic shock who received vasopressin. Id. Anantasit reported that septic shock patients with the TT/TA genotype had statistically significant higher AVP blood levels than those with the AA genotype. Id. at FIG. 2. Anantasit also concluded that patients who had the AA genotype had significantly higher rates of serious adverse events, but that the mechanism of this association requires further investigation.

Therefore, because of the unpredictable nature of pharmaceutical dosing to achieve safety and efficacy, there is a need in the art to better understand the dosing, efficacy and safety of vasopressin administration in patients having the TT, AA and AT genotypes.

SUMMARY

The present disclosure satisfies the above need and relates to methods of treating patients experiencing hypotension, particularly in patients having or evincing the TT, AA, or AT genotype. In light of what was known from the above literature, Applicant surprisingly found that patients with the AA or AT genotype have lower serum concentrations of vasopressin and increased clearance while TT genotype patients exhibited increased serum concentrations and lower vasopressin clearance as compared to the AA or AT genotyped patients. The treatment methods described herein generally comprise determining whether the patient is the TT, AA, or AT genotype, and then administering a dosing regimen of vasopressin based on genotype. The methods of the present invention result in improved survival rates and/or reduction of adverse events in TT, AA, and AT genotype patients who experience acute conditions, such as shock.

In one embodiment, the present disclosure relates to a method of increasing blood pressure in a patient having the AA or AT genotype and experiencing post-cardiotomy shock by administering to such patient a dose of vasopressin that is higher than the currently labeled dose for VASOSTRICT®. Such increased dose may be achieved by increasing one or more of (a) the starting dose; (b) the titration dose; and/or (c) the maximum dose. In some embodiments, the total increased dose is at least 5% higher than the labeled dose for VASOSTRICT®, or about 5% to 40% higher, or about 10% to 30% higher, or about 15% to 25% higher, or about 20% higher, or about 30% higher than the labeled dose for VASOSTRICT®.

In another embodiment, the present disclosure relates to a method of increasing blood pressure in a patient having the AA or AT genotype and experiencing septic shock by administering to such patient a dose of vasopressin that is higher than the currently labeled dose for VASOSTRICT®. Such increased dose may be achieved by increasing one or more of (a) the starting dose; (b) the titration dose; and/or (c) the maximum dose. In some embodiments, the total increased dose is at least 5% higher than the labeled dose for VASOSTRICT®, or about 5% to 40% higher, or about 10% to 30% higher, or about 15% to 25% higher, or about 20% higher, or about 30% higher than the labeled dose for VASOSTRICT®.

The present disclosure further relates to a method of increasing blood pressure in a patient having the TT genotype and experiencing post-cardiotomy shock by administering to such patient a dose of vasopressin that is lower than the currently labeled dose for VASOSTRICT®. Such lowered dose may be achieved by decreasing one or more of (a)

the starting dose; (b) the titration dose; and/or (c) the maximum dose. In some embodiments, the total decreased dose is at least 5% lower than the labeled dose for VASOSTRICT®, or about 5% to 40% lower, or about 10% to 30% lower, or about 15% to 25% lower, or about 20% lower, or about 30% lower than the labeled dose for VASOSTRICT®.

In another embodiment, the present disclosure relates to a method of increasing blood pressure in a patient having the TT genotype and experiencing septic shock by administering to such patient a dose of vasopressin that is lower than the currently labeled dose for VASOSTRICT®. Such lowered dose may be achieved by decreasing one or more of (a) the starting dose; (b) the titration dose; and/or (c) the maximum dose. In some embodiments, the total decreased dose is at least 5% lower than the labeled dose for VASOSTRICT®, or about 5% to 40% lower, or about 10% to 30% lower, or about 15% to 25% lower, or about 20% lower, or about 30% lower than the labeled dose for VASOSTRICT®.

In some aspects, the present disclosure relates to a method of increasing blood pressure in a human patient with post-cardiotomy shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.03 units/minute; and (c) if a target blood pressure is not achieved at the starting dose, titrating the vasopressin dose upward by 0.005 units/minute at intervals of about 10 to 15 minutes up to a maximum dose wherein the maximum dose is at least 5% higher than a maximum dose for a patient who does not have the AA or AT genotype. For example, the starting dose for the patient having the AA or AT genotype is about 0.03 units/minute, and the maximum dose for the patient having the AA or AT genotype is about 0.1 to 0.15 units/minute. Alternatively, the maximum dose for the patient having the AA or AT genotype is about 0.121 units/minute.

In another embodiment, the present disclosure relates to a method of increasing blood pressure in a human patient with septic shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.01 units/minute; and (c) if a target blood pressure is not achieved at the starting dose, titrating the vasopressin dose upward by 0.005 units/minute at intervals of about 10 to 15 minutes up to a maximum dose wherein the maximum dose is at least 5% higher than a maximum dose for a patient who does not have the AA or AT genotype. For example, the starting dose for the patient having the AA or AT genotype is about 0.01 units/minute, and the maximum dose for the patient having the AA or AT genotype is about 0.07 to 0.1 units/minute. In certain aspects, the maximum dose for the patient having the AA or AT genotype is about 0.085 units/minute.

The present disclosure further relates to a method of increasing blood pressure in a human patient with post-cardiotomy shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.03 units/minute; and (c) if a target blood pressure is not achieved at the starting dose, titrating the vasopressin dose upward by 0.005 units/minute at intervals of about 10 to 15 minutes up to a maximum dose wherein the maximum dose is at least 10% higher than a maximum dose for a patient who does not have the AA or AT genotype. For example, the maximum dose for the patient having the AA or AT genotype is about 0.121 units/minute achieved with about 18 continuous titrations in about 3 to 4.5 hours.

In another embodiment, the present disclosure relates to a method of increasing blood pressure in a human patient with septic shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.01 units/minute; and (c) if a target blood pressure is not achieved at the starting dose, titrating the vasopressin dose upward by 0.005 units/minute at intervals of about 10 to 15 minutes up to a maximum dose wherein the maximum dose is at least 10% higher than a maximum dose for a patient who does not have the AA or AT genotype. For example, the maximum dose for the patient having the AA or AT genotype is about 0.085 units/minute achieved with 15 continuous titrations in about 2.5 to 3.75 hours.

In other embodiments, the increased doses needed to successfully treat a AA or AT genotype patient may be linear based on the percent increase in clearance versus an otherwise comparable TT genotype patient. For example, when the percent increase in clearance in a AA or AT genotype patient is about 5%, 10%, 20%, 30%, 40%, 50%, 60%, etc., then the dose is increased linearly by about 5%, 10%, 20%, 30%, 40%, 50%, 60%, etc. In other embodiments, the amount of increased dose needed to maintain target blood pressure is not linearly related to the percent decrease in clearance. For example, when the percent increase in clearance in an AA or AT genotype patient is about 5%, 10%, 20%, 30%, 40%, 50%, 60%, etc., then the dose is increased by about 1% to 50%, or about 2% to 40%, or about 5% to 35%, or about 10% to 30%, or about 15% to 25%.

Additionally, the decreased doses needed to successfully treat a TT genotype patient may be linear based on the percent decrease in clearance versus an otherwise comparable AA/AT genotype patient. For example, when the percent decrease in clearance in a TT genotype patient is about 5%, 10%, 20%, 30%, 40%, 50%, 60%, etc., then the dose is decreased linearly by about 5%, 10%, 20%, 30%, 40%, 50%, 60%, etc. In other embodiments, the amount of decreased dose needed to maintain target blood pressure is not linearly related to the percent decrease in clearance. For example, when the percent decrease in clearance in a TT genotype patient is about 5%, 10%, 20%, 30%, 40%, 50%, 60%, etc., then the dose is decreased by about 1% to 50%, or about 2% to 40%, or about 5% to 35%, or about 10% to 30%, or about 15% to 25%.

Additional embodiments of the present methods, compositions and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. The order of method steps stated herein are non-limiting and may vary yet achieve the objectives of the present invention. In addition, any feature or combination of features may be specifically excluded from any embodiment or aspect. Additional aspects and embodiments are set forth in the following description and claims, particularly when considered in conjunction with the accompanying examples and drawings.

BRIEF DESCRIPTION OF THE DRAWINGS

The foregoing features of embodiments will be more readily understood by reference to the following detailed description, taken with reference to the accompanying drawings, in which.

DETAILED DESCRIPTION

Figure 1:
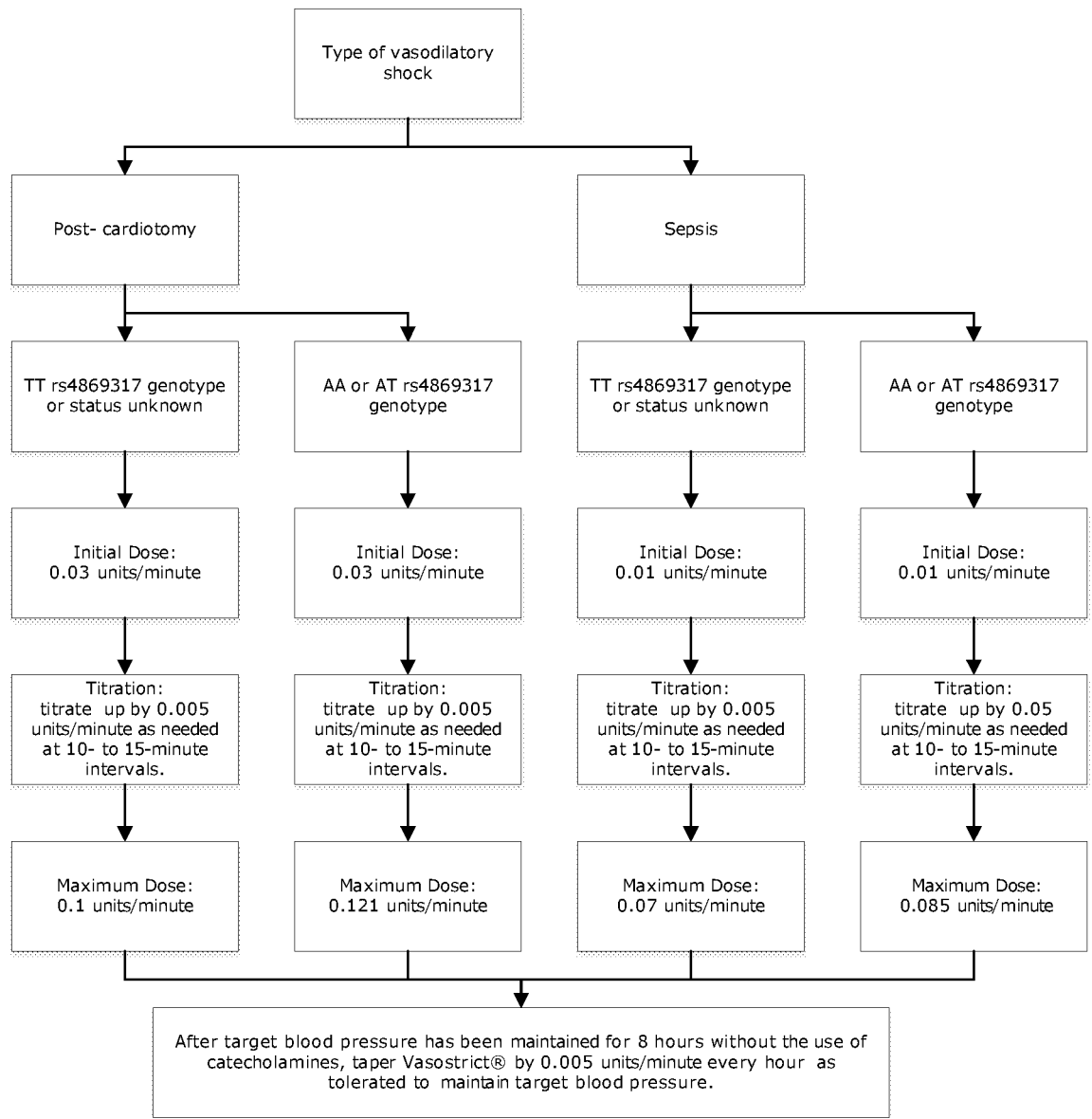
FIG. 1 is a flow chart of a dosing recommendation for patients with the TT rs4869317 Genotype, or AA/AT rs4869317 Genotype, or genotype status unknown.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

A. Introduction

Vasopressin can be used to regulate plasma osmolality and volume, and diseases and conditions related to the same in a patient. For example, vasopressin can be used to modulate blood pressure, and can be indicated in a subject who is hypotensive despite treatment with fluid and catecholamines. Thus, vasopressin can be used in the treatment of, for example, vasodilatory shock, post-cardiotomy shock, sepsis, septic shock, cranial diabetes insipidus, polyuria, nocturia, polydypsia, bleeding disorders, Von Willebrand disease, hemophilia, platelet disorders, cardiac arrest, liver disease, liver failure, hypovolemia, hemorrhage, esophageal variceal hemorrhage, hypertension, pulmonary hypertension, renal disease, polycystic kidney disease, blood loss, injury, hypotension, Meniere disease, uterine myomas, brain injury, and mood disorder. Formulations of vasopressin can be administered to a subject undergoing, for example, surgery or hysterectomy.

The vasopressin formulations described herein are used to achieve a target blood pressure desired by the treating physician. In certain aspects, the target blood pressure for a healthy human adult can range from about 90/60 to about 120/80 mm Hg, or can range from about 80/50 to about 110/70 mm Hg, or from 70/40 to about 100/60. Hypertension can be a blood pressure reading above about 120/80, and can be classified as hypertensive crisis when there is a spike in blood pressure and blood pressure readings reach about 180/110 or higher. Hypertensive crisis can be precipitated by, for example, stroke, myocardial infarction, heart failure, kidney failure, aortic rupture, drug-drug interactions, and eclampsia. Symptoms of hypertensive crisis can include, for example, shortness of breath, angina, back pain, numbness, weakness, dizziness, confusion, change in vision, nausea, and difficulty speaking.

Vasodilatory shock can be characterized by low arterial blood pressure due to decreased systemic vascular resistance. Vasodilatory shock can lead to dangerously low blood pressure levels and can be corrected via administration of catecholamines or vasopressin formulations. Vasodilatory shock can be caused by, for example, sepsis, nitrogen intoxication, carbon monoxide intoxication, hemorrhagic shock, hypovolemia, heart failure, cyanide poisoning, metformin intoxication, and mitochondrial disease.

Post-cardiotomy shock can occur as a complication of cardiac surgery and can be characterized by, for example, inability to wean from cardiopulmonary bypass, poor hemodynamics in the operating room, development of poor hemodynamics post-surgery, and hypotension.

B. Vasopressin Compositions and Dosing

Various vasopressin pharmaceutical formulations are useful in the present invention. Vasopressin can be formulated as an aqueous formulation or a lyophilized powder, which can be diluted or reconstituted just prior to use. Upon dilution or reconstitution, the vasopressin solution may be refrigerated for long-term stability. In some embodiments, a pharmaceutical composition of the invention can be formulated for long-term storage of vasopressin at room temperature in the presence of one or more suitable pharmaceutically-acceptable excipients. The pharmaceutically-acceptable excipient(s) can increase the half-life of vasopressin when stored at any temperature, such as room temperature. The presence of the pharmaceutical excipient(s) can decrease the rate of decomposition of vasopressin at any temperature, such as room temperature. A number of vasopressin formulations and their use are disclosed in U.S. Pat. Nos. 9,925,233; 9,744,209; and 9,750,785, which are incorporated herein by reference.

One non-limiting formulation is vasopressin injection, USP (20 units/mL) for intravenous injection, as described in the prescribing information for VASOSTRICT®. The vasopressin formulations according to the present disclosure may be diluted to a variety of concentrations using normal saline (0.9% sodium chloride) or 5% dextrose in water (D5W), e.g.: About 0.01 to 2 units/mL, or about 0.05 to 1.5 units/mL, or about 0.1 to 1 units/mL, or about 0.06 units/mL, or about 0.07 units/mL, or about 0.08 units/mL, or about 0.09 units/mL, or about 0.1 units/mL, or about 0.2 units/mL, or about 0.3 units/mL, or about 0.4 units/mL, or about 0.5 units/mL, or about 0.6 units/mL, or about 0.7 units/mL, or about 0.8 units/mL, or about 0.9 units/mL, or about 1.0 units/mL, or about 1.1 units/mL, or about 1.2 units/mL, or about 1.3 units/mL, or about 1.4 units/mL, or about 1.5 units/mL, or about 1.5 units/mL, or about 1.6 units/mL, or about 1.7 units/mL, or about 1.8 units/mL, or about 1.9 units/mL, or about 2.0 units/mL.

Generally, according to the present disclosure, depending on patient genotype, a therapeutically effective amount of vasopressin or a pharmaceutically-acceptable salt thereof to maintain a target blood pressure is from about 0.01 units/minute to about 0.15 units/minute. As detailed below, the dosing protocols of AA, AT and TT genotype patients are different from the VASOSTRICT® prescribing information. Such VASOSTRICT® prescribing information states that for post-cardiotomy shock, a starting dose of 0.03 units/minute is employed. For septic shock, a starting dose is 0.01 units/minute. If the target blood pressure response is not achieved, the physician is to titrate up by 0.005 units/minute at 10 to 15 minute intervals. The maximum dose for post-cardiotomy shock is 0.1 units/minute and for septic shock 0.07 units/minute. After target blood pressure has been maintained for 8 hours without the use of catecholamines, the vasopressin dose is tapered by 0.005 units/minute every hour as tolerated to maintain target blood pressure. However, as discussed herein and as established in the Example below, Applicant surprisingly discovered that certain genotypes, such as patients having the AA or AT genotype require higher doses of vasopressin as compared to patients with the TT genotype. Also, TT genotype patients may require lower doses than those in the current VASOSTRICT® label due to their decreased ability to clear vasopressin.

At infusion rates used in vasodilatory shock (i.e., 0.01-0.1 units/minute), the clearance of vasopressin ranges from about 9 to about 25 mL/min/kg. In certain embodiments, such decreased vasopressin clearance is as set forth in Table 1 below.

TABLE 1

An Overview of the Parameters for Treatment of Hypotension Using Vasopressin

| Infusion rate (units/minute) | Concentration at steady state in TT genotype patients | Clearance in TT genotype patients (mL/min/kg) | Concentration at steady state in AA/AT genotype patients | Clearance in AA/AT genotype patients (mL/min/kg) | % change in the pharmacokinetic parameters in AA/AT genotype patients vs. TT genotype patients | % increase in clearance in AA/AT genotype patients vs. TT genotype patients |
|---|---|---|---|---|---|---|
| 0.01 | 1 pmol/L or 3.7 pg/mL | 16 | 0.65 to 0.95 pmol/L or 2.38 to 3.48 pg/mL | 16.8 to 24 | <5%, or about 10%, 15%, 20%, 25%, 30%, 35% | >5%, or about 10%, 15%, 20%, 25%, 30%, 35%, 40%, 45%, 50% |
| 0.02 | 2.5 pmol/L or 9.2 pg/mL | 18 | 1.625 to 2.375 pmol/L or 5.96 to 8.7 pg/mL | 18.9 to 27 | <5%, or about 10%, 15%, 20%, 25%, 30%, 35% | >5%, or about 10%, 15%, 20%, 25%, 30%, 35%, 40%, 45%, 50% |
| 0.03 | 4.70 +/− 4.67 pmol/L or 17.25 +/− 17.14 pg/mL | 19.7 +/− 6.5 | 3.17 +/− 2.10 pmol/L or 11.63 +/− 7.71 pg/mL | 28.7 +/− 17.7 | <33% | ≥46% |
|  | 4.5 pmol/L or 16.5 pg/mL | 20 | 0.45 to 4.4 pmol/L or 1.65 to 1.64 pg/mL | 21-30 | <5%, or about 10%, 15%, 20%, 25%, 30%, 35% | >5%, or about 10%, 15%, 20%, 25%, 30%, 35%, 40%, 45%, 50% |
| 0.05 | 7 pmol/L or 26 pg/mL | 24 | 4.55 to 6.65 pmol/L or 16.9 to 24.7 pg/mL | 25.2 to 36 | <5%, or about 10%, 15%, 20%, 25%, 30%, 35% | >5%, or about 10%, 15%, 20%, 25%, 30%, 35%, 40%, 45%, 50% |
| 0.06 | 8 pmol/L or 29 pg/mL | 26 | 5.2 to 7.6 pmol/L or 18.85 to 27.55 pg/mL | 27.3 to 39 | <5%, or about 10%, 15%, 20%, 25%, 30%, 35% | >5%, or about 10%, 15%, 20%, 25%, 30%, 35%, 40%, 45%, 50% |
| 0.07 | 9 pmol/L or 33 pg/mL | 28 | 5.85 to 8.55 pmol/L or 21.45 to 31.35 pg/mL | 28.4 to 42 | <5%, or about 10%, 15%, 20%, 25%, 30%, 35% | >5%, or about 10%, 15%, 20%, 25%, 30%, 35%, 40%, 45%, 50% |
| 0.08 | 10 pmol/L or 37 pg/mL | 30 | 6.5 to 9.5 pmol/L or 24.05 to 35.15 pg/mL | 31.5 to 45 | <5%, or about 10%, 15%, 20%, 25%, 30%, 35% | >5%, or about 10%, 15%, 20%, 25%, 30%, 35%, 40%, 45%, 50% |

TABLE 1-continued

An Overview of the Parameters for Treatment of Hypotension Using Vasopressin

| Infusion rate (units/minute) | Concentration at steady state in TT genotype patients | Clearance in TT genotype patients (mL/min/kg) | Concentration at steady state in AA/AT genotype patients | Clearance in AA/AT genotype patients (mL/min/kg) | % change in the pharmacokinetic parameters in AA/AT genotype patients vs. TT genotype patients | % increase in clearance in AA/AT genotype patients vs. TT genotype patients |
|---|---|---|---|---|---|---|
| 0.09 | 11 pmol/L or 40 pg/mL | 32 | 7.15 to 10.45 pmol/L or 26 to 38 pg/mL | 33.6 to 48 | <5%, or about 10%, 15%, 20%, 25%, 30%, 35% | >5%, or about 10%, 15%, 20%, 25%, 30%, 35%, 40%, 45%, 50% |
| 0.1 | 12 pmol/L or 44 pg/mL | 35 | 7.8 to 11.4 pmol/L or 28.6 to 41.8 pg/mL | 36.75 to 42.5 | <5%, or about 10%, 15%, 20%, 25%, 30%, 35% | >5%, or about 10%, 15%, 20%, 25%, 30%, 35%, 40%, 45%, 50% |

C. Methods of Treating Patients with the TT, AA, or AT Genotype

The present disclosure generally relates to methods of treating patients experiencing hypotension, particularly in patients having or evincing the TT, AA, or AT genotype. The method generally comprises determining whether the patient is the TT, AA, or AT genotype, and then administering a dosing regimen of vasopressin based on genotype. Such determination is performed as is known in the art, e.g., polymerase chain reaction (PCR), hybridization probe, direct DNA sequencing, spectrophotometry, phenotyping, vasopressinase assay, etc. See, e.g., Young et al., "Deconstructing The Sources Of Genotype-Phenotype Associations In Humans," Science 365(6460): 1396-1400 (Sep. 27, 2019); Edenberg et al., "Laboratory Methods for High-Throughput Genotyping," Cold Spring Harbor Lab. Press, 16:183-193 (2009); Kristensen et al., "High-Throughput Methods for Detection of Genetic Variation," BioTechniques 30:318-332 (February 2001); Kim S. et al., "SNP Genotyping: Technologies and Biomedical Applications," Ann. Rev. Biomed. Eng. 9:289-320 (2007); Ramirez-Exposito et al., "A PCR-RFLP Method For Detection Of The LNPEP Encoding Human Insulin-Regulated Aminopeptidase (IRAP) R54869317 Polymorphism," Indian J. Med. Res. 144(1): 120-123 (July 2016).

In one embodiment, 2-mL blood sample may be collected for each patient prior to, during, or after vasopressin treatment for determination of LNPEP genotype (TT, AA, or AT). Because of the acute nature of the conditions treated with vasopressin, in some embodiments, the genetic screening is performed during treatment, and then the dose is adjusted according to the outcome. Based on the improved dosing regimens based on genotype as described herein, the present invention increases the survival rate (regardless of when the genotyping is done) of patients with acute conditions, including patients with septic shock and post-cardiotomy shock. In some aspects, the survival rate in TT, AA, or AT genotype patients that are administered the doses described herein is improved by at least 5%, 10%, 15%, 20%, or 30%.

Dose Adjustments in AA or AT Genotype Patients

The present disclosure generally relates to a method of treating a hypotensive patient having the AA or AT genotype by infusing a therapeutically effective amount of vasopressin to maintain a target blood pressure that is more than a therapeutically effective amount administered to an otherwise comparable patient who does not have the AA or AT genotype. In certain aspects, the therapeutically effective amount administered to the patient having the AA or AT genotype is about 5%, 10%, 20%, 30%, 40%, 50%, 60%, 70%, 80%, 90%, or 100% more than a therapeutically effective amount administered to an otherwise comparable patient who does not have the AA or AT genotype. In other cases, the patient who does not have the AA or AT genotype has the TT genotype, and is otherwise comparable to the AA or AT genotype patient in terms of age (±5 years), sex, race, BMI (±5%), and creatinine clearance (±10 mL/min.).

In one embodiment, patients are treated with vasopressin according to the dosing recommendation shown in FIG. 1.

In other embodiments, a patient with the AA or AT genotype is administered vasopressin to treat hypotension with a dose (e.g., units/minute) that is higher than the dose (units/minute) currently stated in the prescribing information as approved by the U.S. FDA, for example, the VASOSTRICT® prescribing information. For instance, in a AA or AT genotype patient experiencing post-cardiotomy shock, vasopressin is infused at a rate higher than about 0.1 units/minute to maintain target blood pressure. Alternatively, in a AA or AT genotype patient experiencing septic shock, vasopressin is administered at a rate higher than 0.07 units/minute to maintain target blood pressure. In some aspects, the dose in an AA or AT genotype patient necessary to maintain target blood pressure are about 5%, 10%, 20%, 30%, 40%, 50%, 60%, 70%, 80%, 90% or about 100% higher than currently approved doses of vasopressin.

In another embodiment, the present disclosure relates to AA or AT genotype patients having at least a 5% higher rate of vasopressin clearance (mL/min/kg) compared to TT genotype patients. In such cases, the disclosure relates to a method of treating a hypotensive patient having the AA or AT genotype comprising administering a therapeutically effective amount of vasopressin to maintain target blood pressure that is at least 5% more than a therapeutically effective amount to maintain target blood pressure administered to an otherwise comparable patient who does not have the AA or AT genotype. Alternatively, the therapeutically effective amount of vasopressin to maintain target blood pressure in a AA or AT genotype patient is at least 10%, 20%, 30%, 40%, 50%, 60%, 70%, 80%, 90%, or 100% more than a therapeutically effective amount to maintain target blood pressure administered to an otherwise comparable patient who does not have the AA or AT genotype. In other aspects, such patients who do not have the AA or AT genotype are the TT genotype, and are otherwise comparable to the AA or AT genotype patients in terms of age (±5 years), sex, race, BMI (±5%), and creatinine clearance (±10 mL/min.).

In certain embodiments, the higher doses needed to successfully treat an AA or AT genotype patient may be linear based on the percent increase in clearance versus an otherwise comparable TT genotype patient. For example, when the percent increase in clearance in an AA or AT genotype patient is about 5%, 10%, or 20%, 30%, 40%, 50%, 60%, etc., then the dose is increased linearly by about 5%, 10%, 20%, 30%, 40%, 50%, 60%, etc. In other embodiments, the amount of increased dose needed to maintain target blood pressure is not linearly related to the percent decrease in clearance. For example, when the percent increase in clearance in an AA or AT genotype patient is about 5%, 10%, 20%, 30%, 40%, 50%, 60%, etc., then the dose is increased by about 1% to 50%, or about 2% to 40%, or about 5% to 35%, or about 10% to 30%, or about 15% to 25%.

The present disclosure further relates to a method of treating a population of hypotensive patients having the AA or AT genotype by infusing a therapeutically effective amount of vasopressin to maintain a target blood pressure that is statistically significantly more than a therapeutically effective amount administered to an otherwise comparable patient population who do not have the AA or AT genotype. In certain aspects, the therapeutically effective amount administered to the patients having the AA or AT genotype is about 5%, 10%, 20%, 30%, 40%, 50%, 60%, 70%, 80%, 90%, or 100% more than a therapeutically effective amount administered to an otherwise comparable patients who do not have the AA or AT genotype, wherein such results are statistically significant. In other cases, the patients who do not have the AA or AT genotype have the TT genotype, and are otherwise comparable to the AA or AT genotype patient in terms of age (±5 years), sex, race, BMI (±5%), and creatinine clearance (±10 mL/min.).

In one embodiment, the present disclosure relates to a method of reducing adverse events associated with vasopressin administration in patients with shock (e.g., post-cardiotomy shock or septic shock) by infusing an increased dose of vasopressin to AA or AT patients (or by infusing a decreased dose of vasopressin to TT patients, see below). Adverse events include, but are not limited to, myocardial ischemica, tachyarrythmias (such as Torsade de Pointes), bradyarrythmias, cerebrovascular accident, unexpected cardiac arrest, digital ischemia, mesenteric ischemia, hyponatremia, rhabdomyolysis, and non-specific gastrointestinal symptoms.

Treating Post-Cardiotomy Shock in AA or AT Genotype Patients

The present disclosure relates to a method of increasing blood pressure in a patient having the AA or AT genotype and experiencing post-cardiotomy shock by administering to such patient a dose of vasopressin that is higher than the currently labeled dose for VASOSTRICT®. Such increased dose may be achieved by increasing one or more of the following dosing parameters: (a) the starting dose; (b) the titration dose; and/or (c) the maximum dose. In some embodiments, the total increased dose is at least 5% higher than the labeled dose for VASOSTRICT®, or about 5% to 40% higher, or about 10% to 30% higher, or about 15% to 25% higher, or about 20% higher, or about 30% higher than the labeled dose for VASOSTRICT®. Alternatively, one or two of the three dosing parameters may be increased while the remainder decreased provided that the net total dose of vasopressin is increased by at least 5%.

According to the present disclosure, a therapeutically effective amount of vasopressin or a pharmaceutically-acceptable salt thereof to maintain a target blood pressure in a patient having the AA or AT genotype ranges from about 0.01 units/minute to about 0.2 units/minute. For post-cardiotomy shock, a starting dose in an AA or AT genotype patient ranges from about 0.03 units/minute to about 0.07 units/minute. If the target blood pressure response is not achieved, the physician is to titrate up by about 0.005 units/minute at about 10 to 15 minute intervals. The maximum dose for post-cardiotomy shock in an AA or AT genotype patient is greater than about 0.1 units/minute, or about 0.11 to 0.2 units/minute, or about 0.11 to 0.18 units/minute, or about 0.11 to 0.16 units/minute, or about 0.11 to 0.15 units/minute, or about 0.14 units/minute, or about 0.13 units/minute, or about 0.12 units/minute, or about 0.11 units/minute. After target blood pressure has been maintained for about 8 hours without the use of catecholamines, the vasopressin dose is tapered by about 0.005 units/minute every hour as tolerated to maintain target blood pressure.

Further, in a population of AA or AT genotype patients with post-cardiotomy shock who are treated with a higher dose of vasopressin as compared to TT genotype patients, a statistically significant number of the AA or AT genotype patients have an improved survival rate over TT genotype patients who were not treated with such a higher dose. Such higher dose may be about 5%, 10%, 20%, 30%, 40%, 50%, 60%, 70%, 80%, 90%, or 100% more than a therapeutically effective amount administered to an otherwise comparable patient who does not have the AA or AT genotype.

In some aspects, the present disclosure relates to a method of increasing blood pressure in a human patient with post-cardiotomy shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.03 units/minute or at least 5% higher than a starting dose for a patient who does not have the AA or AT genotype; and (c) if a target blood pressure is not achieved at the starting dose, titrating the vasopressin dose upward by 0.005 units/minute at intervals of about 10 to 15 minutes up to a maximum dose wherein the maximum dose is at least 5% higher than a maximum dose for a patient who does not have the AA or AT genotype. For example, the starting dose for the patient having the AA or AT genotype is about 0.03 units/minute, and the maximum dose for the patient having the AA or AT genotype is about 0.1 to 0.15 units/minute. Alternatively, the maximum dose for the patient having the AA or AT genotype is about 0.121 units/minute.

In another embodiment, the present disclosure relates to a method of increasing blood pressure in a human patient with post-cardiotomy shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.03 units/minute; and (c) if a target blood pressure is not achieved at the starting dose, titrating the vasopressin dose upward by 0.005 units/minute at intervals of about 10 to 15 minutes up to a maximum dose wherein the maximum dose is at least 10% higher than a maximum dose for a patient who does not have the AA or AT genotype. For example, the maximum dose for the patient having the AA or AT genotype is greater than 0.1 units/minute. Alternatively, the maximum dose for the patient having the AA or AT genotype is about 0.121 units/minute.

In another example, as shown in the table below, the maximum dose of vasopressin in an AA or AT genotype patient being treated for post-cardiotomy shock is higher than the currently labeled dose of VASOSTRICT®.

TABLE 2

Treatment of Post-Cardiotomy Shock

| | VASOSTRICT ® Label | AA or AT Genotype Patient |
|---|---|---|
| Starting Dose | 0.03 units/minute | About 0.03 units/minute |
| Titration Dose | 0.005 units/minute at 10- to 15-minute intervals | 0.005 units/minute at 10- to 15-minute intervals |
| Maximum Dose | 0.1 units/minute | About 0.121 units/minute |
| Taper Down† | 0.005 units/minute every hour as tolerated to maintain target blood pressure | 0.005 units/minute every hour as tolerated to maintain target blood pressure |

†After target blood pressure has been maintained for about 8 hours without the use of catecholamines.

Thus, if an AA or AT genotype patient requires a maximum dose of 0.121 units/minute, the patient is started at 0.03 units/minute and titrated up with about 18 titrations of 0.005 units/minute every 10 to 15 minutes (i.e., over about 3 to 4.5 hours).

Treating Septic Shock in AA or AT Genotype Patients

The present disclosure also relates to a method of increasing blood pressure in a patient having the AA or AT genotype and experiencing septic shock by administering to such patient a dose of vasopressin that is higher than the currently labeled dose for VASOSTRICT®. Such increased dose may be achieved by increasing one or more of the following dosing parameters: (a) the starting dose; (b) the titration dose; and/or (c) the maximum dose. In some embodiments, the total increased dose is at least 5% higher than the labeled dose for VASOSTRICT®, or about 5% to 40% higher, or about 10% to 30% higher, or about 15% to 25% higher, or about 20% higher, or about 30% higher than the labeled dose for VASOSTRICT®. Alternatively, one or two of the three dosing parameters may be increased while the remainder decreased provided that the net total dose of vasopressin is increased by at least 5%.

According to the present disclosure, a therapeutically effective amount of vasopressin or a pharmaceutically-acceptable salt thereof to maintain a target blood pressure in a patient having the AA or AT genotype ranges from about 0.01 units/minute to about 0.2 units/minute. For septic shock, a starting dose in an AA or AT genotype patient ranges from about 0.01 units/minute to about 0.05 units/minute. If the target blood pressure response is not achieved, the physician is to titrate up by about 0.005 units/minute at about 10 to 15 minute intervals. After target blood pressure has been maintained for about 8 hours without the use of catecholamines, the vasopressin dose is tapered by about 0.005 units/minute every hour as tolerated to maintain target blood pressure.

In other aspects, the maximum dose for AA or AT genotype patients with septic shock is greater than 0.07 units/minute or about 0.075 to 0.1 units/minute, or about 0.075 to 0.09 units/minute, or about 0.075 to 0.085 units/minute, or about 0.080 units/minute, or about 0.081 units/minute, or about 0.085 units/minute. After target blood pressure has been maintained for about 8 hours without the use of catecholamines, the vasopressin dose is tapered by about 0.005 units/minute every hour as tolerated to maintain target blood pressure.

In another embodiment, in a population of AA or AT genotype patients with septic shock who are treated with a higher dose of vasopressin as compared to TT genotype patients, a statistically significant number of the AA or AT genotype patients have an improved survival rate over AA or AT genotype patients who were not treated with such a higher dose. Such higher dose may be about 5%, 10%, 20%, 30%, 40%, 50%, 60%, 70%, 80%, 90%, or 100% higher than a therapeutically effective amount administered to an otherwise comparable patient who does not have the AA or AT genotype.

The present disclosure further relates to a method of increasing blood pressure in a human patient with septic shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.01 units/minute or at least 5% higher than a starting dose for a patient who does not have the AA or AT genotype; and (c) if a target blood pressure is not achieved at the starting dose, titrating the vasopressin dose upward by 0.005 units/minute at intervals of about 10 to 15 minutes up to a maximum dose wherein the maximum dose is at least 5% higher than a maximum dose for a patient who does not have the AA or AT genotype. For example, the starting dose for the patient having the AA or AT genotype is about 0.01 units/minute, and the maximum dose for the patient having the AA or AT genotype is about 0.07 to 0.09 units/minute. In certain aspects, the maximum dose for the patient having the AA or AT genotype is about 0.085 units/minute.

In another embodiment, the present disclosure relates to a method of increasing blood pressure in a human patient with septic shock, comprising: (a) determining whether the patient has the LNPEP genotype AA or AT; (b) if the patient has the AA or AT genotype, intravenously administering to the patient a pharmaceutical formulation comprising vasopressin at a starting dose of about 0.01 units/minute; and (c) if a target blood pressure is not achieved at the starting dose, titrating the vasopressin dose upward by 0.005 units/minute at intervals of about 10 to 15 minutes up to a maximum dose wherein the maximum dose is at least 10% higher than a maximum dose for a patient who does not have the AA or AT genotype. For example, the maximum dose for the patient having the AA or AT genotype is about 0.07 to 0.09 units/minute. In certain aspects, the maximum dose for the patient having the AA or AT genotype is about 0.085 units/minute.

In one example, as shown in the table below, the maximum dose of vasopressin in an AA or AT genotype patient being treated for septic shock is higher than the currently labeled dose of VASOSTRICT®.

TABLE 3

Treatment of Septic Shock

| | VASOSTRICT ® Label | AA or AT Genotype Patient |
|---|---|---|
| Starting Dose | 0.01 units/minute | About 0.01 units/minute |
| Titration Dose | 0.005 units/minute at 10- to 15-minute intervals | 0.005 units/minute at 10- to 15-minute intervals |
| Maximum Dose | 0.07 units/minute | About 0.081 or about 0.085 units/minute |
| Taper Down† | 0.005 units/minute every hour as tolerated to maintain target blood pressure | 0.005 units/minute every hour as tolerated to maintain target blood pressure |

†After target blood pressure has been maintained for about 8 hours without the use of catecholamines.

Thus, if an AA or AT genotype patient requires a maximum dose of 0.085 units/minute, the patient may be started at 0.01 units/minute and titrated up with about 15 titrations of 0.005 units/minute every 10 to 15 minutes (i.e., over about 2.5 to 3.75 hours).

Dose Adjustments in TT Genotype Patients

The present disclosure generally relates to a method of treating a hypotensive patient having the TT genotype by infusing a therapeutically effective amount of vasopressin to maintain a target blood pressure that is less than a therapeutically effective amount administered to an otherwise comparable patient who does not have the TT genotype. In certain aspects, the therapeutically effective amount administered to the patient having the TT genotype is about 5%, 10%, 20%, 30%, 40%, 50%, 60%, 70%, 80%, 90%, or 100% less than a therapeutically effective amount administered to an otherwise comparable patient who does not have the TT genotype. In other cases, the patient who does not have the TT genotype has either the AA or AT genotype, and is otherwise comparable to the TT genotype patient in terms of age (±5 years), sex, race, BMI (±5%), and creatinine clearance (±10 mL/min.).

Figure 2:
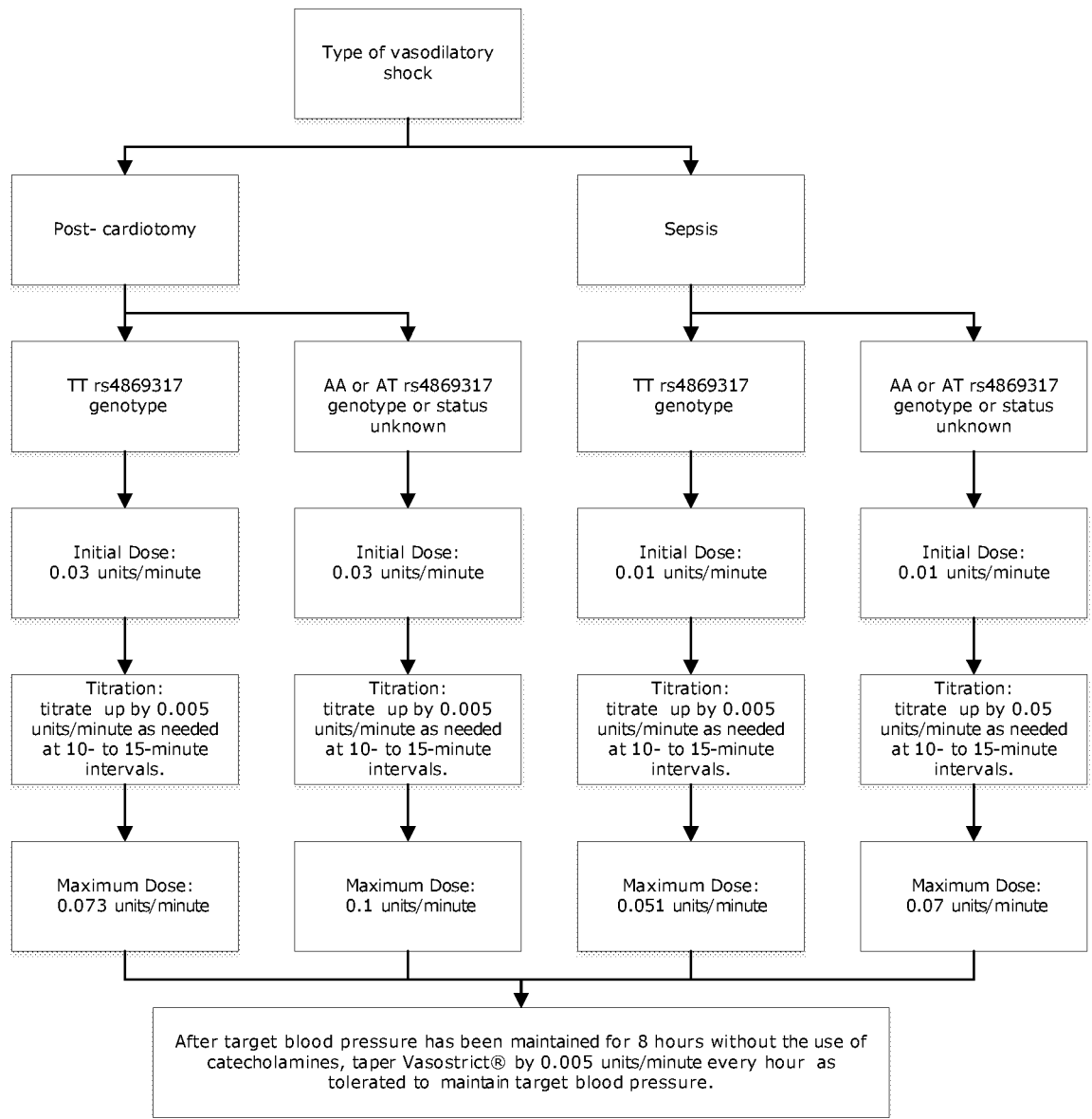
FIG. 2 is a flow chart of a dosing recommendation for patients with the TT rs4869317 Genotype, or AA/AT rs4869317 Genotype, or genotype status unknown.

In one embodiment, patients are treated with vasopressin according to the dosing recommendation shown in FIG. 2.

In other embodiments, a patient with the TT genotype is administered vasopressin to treat hypotension with a dose (e.g., units/minute) that is less than the dose (units/minute) currently stated in the prescribing information as approved by the U.S. FDA, for example, the VASOSTRICT® prescribing information. For instance, in a TT genotype patient experiencing post-cardiotomy shock, vasopressin is infused at a rate less than about 0.1 units/minute to maintain target blood pressure. Alternatively, in a TT genotype patient experiencing septic shock, vasopressin is administered at a rate less than 0.07 units/minute to maintain target blood pressure. In some aspects, the dose in a TT genotype patient necessary to maintain target blood pressure are about 5%, 10%, 20%, 30%, 40%, 50%, 60%, 70%, 80%, 90% or about 100% less than currently approved doses of vasopressin.

In another embodiment, the present disclosure relates to TT genotype patients having at least a 5% lower rate of vasopressin clearance (mL/min/kg) compared to AA or AT genotype patients. In such cases, the disclosure relates to a method of treating a hypotensive patient having the TT genotype comprising administering a therapeutically effective amount of vasopressin to maintain target blood pressure that is at least 5% less than a therapeutically effective amount to maintain target blood pressure administered to an otherwise comparable patient who does not have the TT genotype. Alternatively, the therapeutically effective amount of vasopressin to maintain target blood pressure in a TT genotype patient is at least 10%, 20%, 30%, 40%, 50%, 60%, 70%, 80%, 90%, or 100% less than a therapeutically effective amount to maintain target blood pressure administered to an otherwise comparable patient who does not have the TT genotype. In other aspects, such patients who do not have the TT genotype are either AA or AT genotype, and are otherwise comparable to the TT genotype patients in terms of age (±5 years), sex, race, BMI (±5%), and creatinine clearance (±10 mL/min.).

In certain embodiments, the decreased doses needed to successfully treat a TT genotype patient may be linear based on the percent decrease in clearance versus an otherwise comparable AA/AT genotype patient. For example, when the percent decrease in clearance in a TT genotype patient is about 5%, 10%, or 20%, 30%, 40%, 50%, 60%, etc., then the dose is decreased linearly by about 5%, 10%, 20%, 30%, 40%, 50%, 60%, etc. In other embodiments, the amount of decreased dose needed to maintain target blood pressure is not linearly related to the percent decrease in clearance. For example, when the percent decrease in clearance in a TT genotype patient is about 5%, 10%, 20%, 30%, 40%, 50%, 60%, etc., then the dose is decreased by about 1% to 50%, or about 2% to 40%, or about 5% to 35%, or about 10% to 30%, or about 15% to 25%.

The present disclosure further relates to a method of treating a population of hypotensive patients having the TT genotype by infusing a therapeutically effective amount of vasopressin to maintain a target blood pressure that is statistically significantly less than a therapeutically effective amount administered to an otherwise comparable patient population who do not have the TT genotype. In certain aspects, the therapeutically effective amount administered to the patients having the TT genotype is about 5%, 10%, 20%, 30%, 40%, 50%, 60%, 70%, 80%, 90%, or 100% less than a therapeutically effective amount administered to an otherwise comparable patients who do not have the TT genotype, wherein such results are statistically significant. In other cases, the patients who do not have the TT genotype have either the AA or AT genotype, and are otherwise comparable to the TT genotype patient in terms of age (±5 years), sex, race, BMI (±5%), and creatinine clearance (±10 mL/min.).

Treating Post-Cardiotomy Shock in TT Genotype Patients

The present disclosure further relates to a method of increasing blood pressure in a patient having the TT genotype and experiencing post-cardiotomy shock by administering to such patient a dose of vasopressin that is lower than the currently labeled dose for VASOSTRICT®. Such lowered dose may be achieved by decreasing one or more of the following dosing parameters: (a) the starting dose; (b) the titration dose; and/or (c) the maximum dose. In some embodiments, the total decreased dose is at least 5% lower than the labeled dose for VASOSTRICT®, or about 5% to 40% lower, or about 10% to 30% lower, or about 15% to 25% lower, or about 20% lower, or about 30% lower than the labeled dose for VASOSTRICT®. Alternatively, one or two of the three dosing parameters may be decreased while the remainder increased provided that the net total dose of vasopressin is decreased by at least 5%.

Further, in a population of TT genotype patients with post-cardiotomy shock who are treated with a decreased dose of vasopressin as compared to AA/AT genotype patients, a statistically significant number of the TT genotype patients have an improved survival rate over TT genotype patients who were not treated with such a decreased dose. Such decreased dose may be about 5%, 10%, 20%, 30%, 40%, 50%, 60%, 70%, 80%, 90%, or 100% less than a therapeutically effective amount administered to an otherwise comparable patient who does not have the TT genotype.

In another example, as shown in the table below, the maximum dose of vasopressin in an TT genotype patient being treated for post-cardiotomy shock is lower than the currently labeled dose of VASOSTRICT®.

TABLE 4

Treatment of Post-Cardiotomy Shock

| | VASOSTRICT ® Label | TT Genotype Patient |
|---|---|---|
| Starting Dose | 0.03 units/minute | About 0.03 units/minute |
| Titration Dose | 0.005 units/minute at 10- to 15-minute intervals | 0.005 units/minute at 10- to 15-minute intervals |
| Maximum Dose | 0.1 units/minute | About 0.073 units/minute |
| Taper Down† | 0.005 units/minute every hour as tolerated to maintain target blood pressure | 0.005 units/minute every hour as tolerated to maintain target blood pressure |

†After target blood pressure has been maintained for about 8 hours without the use of catecholamines.

Thus, if a TT genotype patient requires a maximum dose of 0.073 units/minute, the patient is started at 0.03 units/minute and titrated up with about 9 titrations of 0.005 units/minute every 10 to 15 minutes (i.e., over about 1.4 to 2.2 hours).

Treating Septic Shock in TT Genotype Patients

In another embodiment, the present disclosure relates to a method of increasing blood pressure in a patient having the TT genotype and experiencing septic shock by administering to such patient a dose of vasopressin that is lower than the currently labeled dose for VASOSTRICT®. Such lowered dose may be achieved by decreasing one or more of the following dosing parameters: (a) the starting dose; (b) the titration dose; and/or (c) the maximum dose. In some embodiments, the total decreased dose is at least 5% lower than the labeled dose for VASOSTRICT®, or about 5% to 40% lower, or about 10% to 30% lower, or about 15% to 25% lower, or about 20% lower, or about 30% lower than the labeled dose for VASOSTRICT®. Alternatively, one or two of the three dosing parameters may be decreased while the remainder increased provided that the net total dose of vasopressin is decreased by at least 5%.

In another embodiment, in a population of TT genotype patients with septic shock who are treated with a decreased dose of vasopressin as compared to AA/AT genotype patients, a statistically significant number of the TT genotype patients have an improved survival rate over TT genotype patients who were not treated with such a decreased dose. Such decreased dose may be about 5%, 10%, 20%, 30%, 40%, 50%, 60%, 70%, 80%, 90%, or 100% less than a therapeutically effective amount administered to an otherwise comparable patient who does not have the TT genotype.

Further, as shown in the table below, the maximum dose of vasopressin in an TT genotype patient being treated for septic shock is lower than the currently labeled dose of VASOSTRICT®.

TABLE 5

Treatment of Septic Shock

|  | VASOSTRICT® Label | TT Genotype Patient |
|---|---|---|
| Starting Dose | 0.01 units/minute | About 0.01 units/minute |
| Titration Dose | 0.005 units/minute at 10- to 15-minute intervals | 0.005 units/minute at 10- to 15-minute intervals |
| Maximum Dose | 0.07 units/minute | About 0.051 units/minute |
| Taper Down† | 0.005 units/minute every hour as tolerated to maintain target blood pressure | 0.005 units/minute every hour as tolerated to maintain target blood pressure |

†After target blood pressure has been maintained for about 8 hours without the use of catecholamines.

Thus, if a TT genotype patient requires a maximum dose of 0.051 units/minute, the patient is started at 0.01 units/minute and titrated up with about 9 titrations of 0.005 units/minute every 10 to 15 minutes (i.e., over about 1.5 to 2 hours).

D. Kits, Products and Instructions for Use

The vasopressin formulations described herein may be packaged in a variety of dosage forms, such as, for example, vials, ampoules, syringes, bags and bottles suitable for parenteral products. Such dosage forms will include instructions for use and administration (package insert). In one embodiment, there is a provided a vasopressin formulation (20 units/mL) with a package insert comprising the dosing recommendation information shown in FIG. 1. In another embodiment, there is provided a vasopressin formulation (20 units/mL) with a package insert comprising the dosing recommendation information shown in FIG. 2.

In yet another embodiment, the vasopressin dosage form is provided with a package insert comprising the following information:

|  | Post-cardiotomy shock | | | Septic shock | | |
|---|---|---|---|---|---|---|
|  | Starting Dose | Titrating Dose | Maximum Dose | Starting Dose | Titrating Dose | Maximum Dose |
| Genotype Unknown | 0.03 U/min | 0.005 Units/min every 10 to 15 min | 0.1 U/min (achieved with 14 continuous titrations in 2.3-3.5 hours) | 0.01 U/min | 0.005 U/min every 10 to 15 min | 0.07 U/min (achieved with 12 continuous titrations in 2-3 hours) |
| AA/AT Genotype | 0.03 U/min | 0.005 U/min every 10 to 15 min | 0.121 U/min (achieved with 18 continuous titrations, in 3-4.5 hours) | 0.01 U/min | 0.005 U/min every 10 to 15 min | 0.085 U/min (achieved with 15 continuous titrations, in 2.5-3.75 hours) |
| TT Genotype | 0.03 U/min | 0.005 U/min every 10 to 15 min | 0.073 U/min (achieved with 9 continuous titrations, in 1.4-2.2 hours) | 0.01 U/min | 0.005 U/min every 10 to 15 min | 0.051 U/min (achieved with 9 continuous titrations, in 1.4-2 hours) |

Alternatively, the vasopressin dosage form may be provided with a package insert comprising the following information:

|  | Post-cardiotomy shock | | | Septic shock | | |
| --- | --- | --- | --- | --- | --- | --- |
|  | Starting Dose | Titrating Dose | Maximum Dose | Starting Dose | Titrating Dose | Maximum Dose |
| TT Genotype or Genotype Unknown | 0.03 U/min | 0.005 Units/min every 10 to 15 min | 0.1 U/min (achieved with 14 continuous titrations in 2.3-3.5 hours) | 0.01 U/min | 0.005 U/min every 10 to 15 min | 0.07 U/min (achieved with 12 continuous titrations in 2-3 hours) |
| AA/AT Genotype | 0.03 U/min | 0.005 U/min every 10 to 15 min | 0.121 U/min (achieved with 18 continuous titrations, in 3-4.5 hours) | 0.01 U/min | 0.005 U/min every 10 to 15 min | 0.085 U/min (achieved with 15 continuous titrations, in 2.5-3.75 hours) |

In another alternative embodiment, the vasopressin dosage form may be provided with a package insert comprising the following information:

|  | Post-cardiotomy shock | | | Septic shock | | |
| --- | --- | --- | --- | --- | --- | --- |
|  | Starting Dose | Titrating Dose | Maximum Dose | Starting Dose | Titrating Dose | Maximum Dose |
| AA/AT Genotype Genotype Unknown | 0.03 U/min | 0.005 Units/min every 10 to 15 min | 0.1 U/min (achieved with 14 continuous titrations in 2.3-3.5 hours) | 0.01 U/min | 0.005 U/min every 10 to 15 min | 0.07 U/min (achieved with 12 continuous titrations in 2-3 hours) |
| TT Genotype | 0.03 U/min | 0.005 U/min every 10 to 15 min | 0.073 U/min (achieved with 9 continuous titrations, in 1.4-2.2 hours) | 0.01 U/min | 0.005 U/min every 10 to 15 min | 0.051 U/min (achieved with 9 continuous titrations, in 1.4-2 hours) |

Example—Effect of Plasma Clearance of Vasopressin in Subjects with the TT Genotype Versus Those with the AA/AT Genotype Introduction and Study Groups The primary objective of this study was to evaluate differences in plasma clearance of vasopressin following IV administration in subjects with the TT genotype (rs4869317) versus those with the AA/AT genotype of the LNPEP gene in healthy volunteers. The secondary objective of the study was to assess the safety and tolerability of vasopressin in healthy volunteers. This was a Phase 1, open-label, 2-arm, parallel group, PK study in healthy volunteers. Approximately 48 healthy male and female subjects were enrolled at a single center in the United States to achieve at least 19 evaluable subjects per genotype group. The study comprised a screening period, a treatment period, and a follow-up phone call.

Subjects were screened for general good health over a 28-day period. Screening evaluations included medical history, physical examination, vital sign measurement, 12-lead electrocardiogram (ECG), and clinical laboratory testing (hematology, serum chemistry, and urinalysis). In addition, subjects were advised of the diet and medication restrictions and agreed to conform to them.

As a part of screening, the LNPEP genotype (TT or AA/AT) of the subjects was determined. The target enrollment was 24 subjects with the SNP rs4869317 (TT genotype). As the control group, 24 subjects with the AA/AT genotype were approximately matched with respect to age (±5 years), sex, race, BMI (±5%), and creatinine clearance (±10 mL/min). An effort was made to enroll at least 4 female subjects in each genotype group. Subjects were matched during screening and confirmed at check-in on Day −2. Subjects were enrolled for participation in 2 genotype groups of a minimum size of 24 subjects per genotype group in order to meet a minimum of 19 evaluable subjects per genotype group.

Dosing and PK Methodology

A dose of 200 µU/kg/min vasopressin (VASOSTRICT®) was used for this healthy volunteer PK study. The dose roughly corresponds to 0.012 units/minute for a 60 kg individual. This value is approximately equal to the starting dose of 0.01 units/minute in the VASOSTRICT® prescribing information. Clearance in healthy volunteers (15 mL/min/kg) at the vasopressin dose of 200 µU/kg/minute planned for study is within this range. Blood samples for PK analysis were drawn at baseline and 5, 15, 30, and 60 minutes following infusion. If TT genotyped subjects cleared vasopressin at a faster rate, patients of this genotype may benefit from an altered dosing regimen.

According to the VASOSTRICT® prescribing information, the apparent half-life of vasopressin at these levels is <10 minutes, and is primarily determined by LNPEP (also known as vasopressinase). Vasopressin is predominantly metabolized and only about 6% of the dose is excreted unchanged in urine (VASOSTRICT® prescribing information 2019). Animal experiments suggest that the metabolism of vasopressin is primarily by liver and kidney. Serine protease, carboxipeptidase, and disulfide oxido-reductase cleave vasopressin at sites relevant for the pharmacological activity of the hormone. Thus, the generated metabolites are not expected to retain important pharmacological activity. Id.

Subjects who meet all inclusion and none of the exclusion criteria received vasopressin continuous IV infusion at a constant rate of 200 µU/kg/min for 60 minutes on Day 1. To minimize orthostatic hypotension, subjects remained supine throughout the duration of the infusion. Eligible subjects were admitted to the clinical unit on Day −2, i.e., two days prior to dosing, to ensure adequate hydration and to standardize sodium intake. Vasopressin levels were also be determined during this period. Subjects remained confined until completion of all study procedures. While in the clinical unit, subjects were fed a standard diet with a dietary sodium intake limited to 2300 mg per day and drank no less than 1.0 to 1.5 L of water per day in addition to usual consumed beverages. Any subject who did not have a sodium level or plasma osmolality within the laboratory's normal reference range (or who was found to violate any of the other inclusion or exclusion criteria) was discharged from the study prior to dosing.

Study drug was administered on the morning of Day 1 under standard fasting conditions (minimum of 10-hour overnight fast). Passive telemetry monitoring occurred during the infusion. One hour prior to dosing, each subject was given an oral water load of 20 mL/kg to be consumed within 30 minutes. Thereafter, a second 20 mL/kg volume of water was made available. Subjects continued to drink water at regular intervals through the next 90 minutes (end of the infusion). Subjects were asked to pass urine spontaneously within 15 minutes prior to the start of infusion. The fasting restriction continued until the end of the infusion.

Subjects remained in the clinical unit after the end of the infusion and were discharged the following day (Day 2). Subjects were discharged following completion of all assessments barring any need for continued medical monitoring. A follow-up phone call with the subject occurred after 3±1 days to collect adverse events (AEs) and concomitant medications. Pharmacokinetic and safety endpoints were evaluated in the study. Subjects were confined to the clinical unit from Day −2 until discharge on Day 2. The duration of the study, excluding Screening, was approximately 8 days.

Safety and tolerability endpoints included monitoring and recording of adverse events (AEs), clinical laboratory test results (hematology, serum chemistry, and urinalysis), vital sign measurements, 12-lead ECG results, and physical examination findings. For all safety assessments, the investigator determined whether results were clinically significant, defined as any variation in a result that has medical relevance and may result in an alteration in medical care (e.g., active observation, diagnostic measures, or therapeutic measures). If clinical significance was noted, the result and reason for significance were documented and an AE reported on the AE page of the subject's electronic case report form (eCRF). The investigator monitored the subject until the result had reached the reference range or the result at screening, or until the investigator determined that follow-up is no longer medically necessary.

Results

As shown in Tables 6 and 7 below, TT genotyped patients experienced lower vasopressin clearance and higher vasopressin plasma concentrations than AA/AT genotyped patients.

TABLE 6

Descriptive Statistics of Vasopressin Clearance

| Genotype | No. of Subjects | CL (Mean) | CL (SD) | CL (Median) | CL (Min) | CL (Max) |
|---|---|---|---|---|---|---|
| AA/AT | 12 | 17.37 | 7.796 | 15.02 | 9.1 | 37.3 |
| TT | 12 | 13.84 | 4.439 | 13.99 | 4.4 | 22.0 |

Notes:
Clearance Unit = mL/min/Kg

TABLE 7

Descriptive Statistics of Steady State Plasma Concentration of Vasopressin

| Genotype | No. of Subjects | Css (Mean)† | Css (SD) | Css (Median) | Css (Min) | Css (Max) |
|---|---|---|---|---|---|---|
| AA/AT | 12 | 25.042 | 8.9539 | 25.1 | 10.1 | 41.4 |
| TT | 12 | 31.867 | 18.1265 | 27.05 | 17.1 | 86.1 |

Notes:
Concentration Unit = pg/mL
Css = concentration at steady state

Based on these data, the mean clearance in TT patients was about 20% less than that of AA/AT patients. The mean steady state plasma concentration in TT patients was about 27.4% higher than that of AA/AT patients.

The effect of rs4869317 genotype on plasma levels of vasopressin were evaluated in a healthy volunteer pharmacokinetic study. As shown below in Table 8, after a 60 minute continuous intravenous infusion of VASOSTRICT® at a constant rate of 200 µU/kg/min, healthy volunteers with AA/AT rs4869317 genotype (n=12) showed 21.42% lower steady state concentration and 25.5% higher plasma clearance values than TT rs4869317 genotype (n=12). Therefore, when the rs4869317 genotype information is available to the treating physician, it can assist in selection of doses as described elsewhere herein.

TABLE 8

Steady State Concentrations and Total Plasma Clearance in rs4869317 genotypes

| | TT rs4869317 genotype (n = 12) | AA/AT rs4869317 genotype (n = 12) |
|---|---|---|
| Steady State Concentration at 60 minutes (Css), pg/mL | 31.867 +/− 18.1265 | 25.042 +/− 8.9539 |
| Total Plasma Clearance (CL) Value, mL/min/kg | 13.84 +/− 4.439 | 17.37 +/− 7.796 |

Accordingly, based on the above results, some recommended doses of vasopressin based on genotype are as follows. Such recommended doses are shown compared to the current labeled dosing for VASOSTRICT®.

TABLE 7

| | Post-cardiotomy shock | | | Septic shock | | |
|---|---|---|---|---|---|---|
| | Starting Dose | Titrating Dose | Maximum Dose | Starting Dose | Titrating Dose | Maximum Dose |
| Vasostrict ® Package Insert Genotype Unknown | 0.03 U/min | 0.005 Units/min every 10 to 15 min | 0.1 U/min (achieved with 14 continuous titrations in 2.3-3.5 hours) | 0.01 U/min | 0.005 U/min every 10 to 15 min | 0.07 U/min (achieved with 12 continuous titrations in 2-3 hours) |
| AA/AT Genotype | 0.03 U/min | 0.005 U/min every 10 to 15 min | 0.121 U/min (achieved with 18 continuous titrations, in 3-4.5 hours) | 0.01 U/min | 0.005 U/min every 10 to 15 min | 0.085 U/min (achieved with 15 continuous titrations, in 2.5-3.75 hours) |
| TT Genotype | 0.03 U/min | 0.005 U/min every 10 to 15 min | 0.073 U/min (achieved with 9 continuous titrations, in 1.4-2.2 hours) | 0.01 U/min | 0.005 U/min every 10 to 15 min | 0.051 U/min (achieved with 9 continuous titrations, in 1.4-2 hours) |

The embodiments described herein are intended to be merely exemplary. Persons skilled in the art will understand that variations and modifications may be made without departing from the scope of the invention encompassed by the claims below.

What is claimed is:

1. A method of increasing blood pressure to a target blood pressure in a human patient with septic shock wherein the patient has an LNPEP AA or AT rs4869317 genotype, the method comprising: intravenously administering to the patient a pharmaceutical formulation comprising vasopressin at a starting dose of 0.01 units/minute and titrating the dose up by 0.005 units/minute at 10 to 15 minute intervals to maintain the target blood pressure, wherein the maximum dose is 0.085 units/minute.

2. The method of claim 1 wherein the pharmaceutical formulation further comprises sodium acetate buffer.

3. The method of claim 1 wherein the pharmaceutical formulation, prior to dilution, comprises vasopressin 20 units/mL and has a pH of 3.7 to 3.9.

4. The method of claim 1 wherein the patient has at least a 5% higher rate of vasopressin clearance (mL/min/kg) compared to an LNPEP TT rs4869317 genotype patient who receives the same dose.

5. The method of claim 1 wherein the patient has at least a 10% higher rate of vasopressin clearance (mL/min/kg) compared to an LNPEP TT rs4869317 genotype patient who receives the same dose.

6. The method of claim 1 wherein the patient and has about a 25% higher rate of vasopressin clearance (mL/min/kg) compared to an LNPEP TT rs4869317 genotype patient who receives the same dose.

* * * * *